United States Patent
Sadeghi et al.

(10) Patent No.: US 7,304,741 B2
(45) Date of Patent: Dec. 4, 2007

(54) PESTICIDE DETECTOR AND METHOD

(75) Inventors: Darius Akbar Sadeghi, Carmel, CA (US); Herbert L Berman, Los Altos Hills, CA (US)

(73) Assignee: Bio-Chek LLC, Carmel, CA (US)

( * ) Notice: Subject to any disclaimer, the term of this patent is extended or adjusted under 35 U.S.C. 154(b) by 0 days.

(21) Appl. No.: 11/456,292

(22) Filed: Jul. 10, 2006

(65) Prior Publication Data

US 2006/0244962 A1     Nov. 2, 2006

Related U.S. Application Data

(63) Continuation-in-part of application No. 11/062,048, filed on Feb. 18, 2005.

(51) Int. Cl.
*G01N 21/25*     (2006.01)
(52) U.S. Cl. .................................................. 356/417
(58) Field of Classification Search ................. 356/417
See application file for complete search history.

(56) References Cited

U.S. PATENT DOCUMENTS

| | | | |
|---|---|---|---|
| 4,650,336 A * | 3/1987 | Moll ......................... 356/417 |
| 4,666,672 A | 5/1987 | Miller |
| 4,771,006 A | 9/1988 | Miller |
| 5,166,813 A | 11/1992 | Metz |
| 5,846,753 A | 12/1998 | Akkara |
| 5,994,707 A | 11/1999 | Mendoza |
| 6,052,187 A * | 4/2000 | Krishnan et al. ........... 356/364 |
| 6,201,989 B1 * | 3/2001 | Whitehead et al. ....... 250/461.2 |
| 6,343,168 B1 | 1/2002 | Murphy |
| 6,571,118 B1 | 5/2003 | Utzinger |
| 6,792,395 B2 | 9/2004 | Roberts |
| 2003/0048445 A1 * | 3/2003 | Tokhtuev et al. ........... 356/408 |
| 2003/0160182 A1 * | 8/2003 | Petrich et al. ........... 250/458.1 |
| 2003/0206301 A1 * | 11/2003 | Cline et al. .................. 356/417 |
| 2004/0199079 A1 * | 10/2004 | Chuck et al. ................ 600/477 |
| 2005/0030533 A1 * | 2/2005 | Treado ........................ 356/318 |
| 2006/0208171 A1 * | 9/2006 | Holland ...................... 250/221 |

OTHER PUBLICATIONS

Booksh, Excitation Emission Matrix Fluorescence, Booksh Group Home Page, Arizona State University, www.public.asu.edu/booksh/eem.htm, Jan. 14, 2005.

(Continued)

*Primary Examiner*—Gregory J. Toatley, Jr.
*Assistant Examiner*—Kara E Geisel
(74) *Attorney, Agent, or Firm*—Edward S. Wright (57) ABSTRACT

Highly portable, handheld instrument which can be pointed at the produce to be checked. Light from a source within the instrument is directed onto the produce to induce fluorescent emission from the produce, and fluorescent emissions from the produce are monitored with a detector within the instrument to detect the presence of pesticide residue on the produce. The light from the source is filtered to selectively pass light of a wavelength which induces maximum fluorescent emission from the pesticide to be detected, and the emissions from the produce are filtered to selectively pass emissions having a spectral content characteristic of the pesticide to be detected.

23 Claims, 9 Drawing Sheets

OTHER PUBLICATIONS

C & L Instruments, Inc., Optics of a Fluorescence Microscope, www.fluorescence.com/tutorial/fm-optic.htm, no date.

Freudenrich, Fluorescence Microscopy, How Light Microscopes Work, www.science.howstuffworks.com/light-microscope4.htm, no date.

Jiji et al., Excitation-Emission Matrix Fluorescence based Determination of Carbamate Pesticides and Polycyclic Aromatic Hydrocarbons, Analytica Chimica Acta 397, 1999, 61-72.

Jiji et al., Application of PARAFAC for Calibration with Excitation-Emission Matrix Fluorescence Spectra of Three Classes of Environmental Pollutants, Journal of Chemometrics, 2000, 171-185.

* cited by examiner

PESTICIDE DETECTOR AND METHOD

RELATED APPLICATIONS

Continuation-in-Part of Ser. No. 11/062,048, filed Feb. 18, 2005.

BACKGROUND OF THE INVENTION

1. Field of Invention

This invention pertains generally to the detection of pesticides and, more particularly, to a handheld instrument and method which are particularly suitable for detecting pesticides on lettuce and other produce.

2. Related Art

Organic farming has been one of the fastest growing segments of American agriculture in recent years, and many people prefer organic produce because of its superior taste and quality. Organic farmers are not allowed to use synthetic pesticides or fertilizers, and organically grown produce contains significantly lower levels of pesticide residues than conventionally grown produce. With its more stringent growing requirements, popularity among consumers, and relatively limited availability, organic produce generally commands a higher price than conventional produce.

Organic produce is currently checked for pesticide residue by washing the produce with water and then sending a sample of the water to a laboratory for analysis. That is a time consuming and expensive process and one which is not suitable for in situ checking to see if a given load of produce has, in fact, been organically grown.

Heretofore, there have been some attempts to provide portable instruments for checking produce for the presence of pesticide residue through fluorescence spectroscopy in the field. Such attempts still require the use of an aqueous sample which is placed in a cuvette and analyzed in a spectrometer. While such instruments avoid the need to send the sample to a laboratory, the use of the aqueous sample is still time consuming and cumbersome.

OBJECTS AND SUMMARY OF THE INVENTION

It is, in general, an object of the invention to provide a new and improved instrument and method for detecting pesticides on lettuce and other produce.

Another object of the invention is to provide an instrument and method of the above character in which the instrument is highly portable and handheld.

These and other objects are achieved in accordance with the invention by providing a highly portable, handheld instrument which can be pointed at the produce to be checked, directing light from a source within the instrument onto the produce to induce fluorescent emission from the produce, and monitoring fluorescent emissions from the produce with a detector within the instrument to detect the presence of pesticide residue on the produce. The light from the source is filtered to selectively pass light of a wavelength which induces maximum fluorescent emission from the pesticide to be detected, and the emissions from the produce are filtered to selectively pass emissions having a spectral content characteristic of the pesticide to be detected.

DETAILED DESCRIPTION

Figures 1, 2:
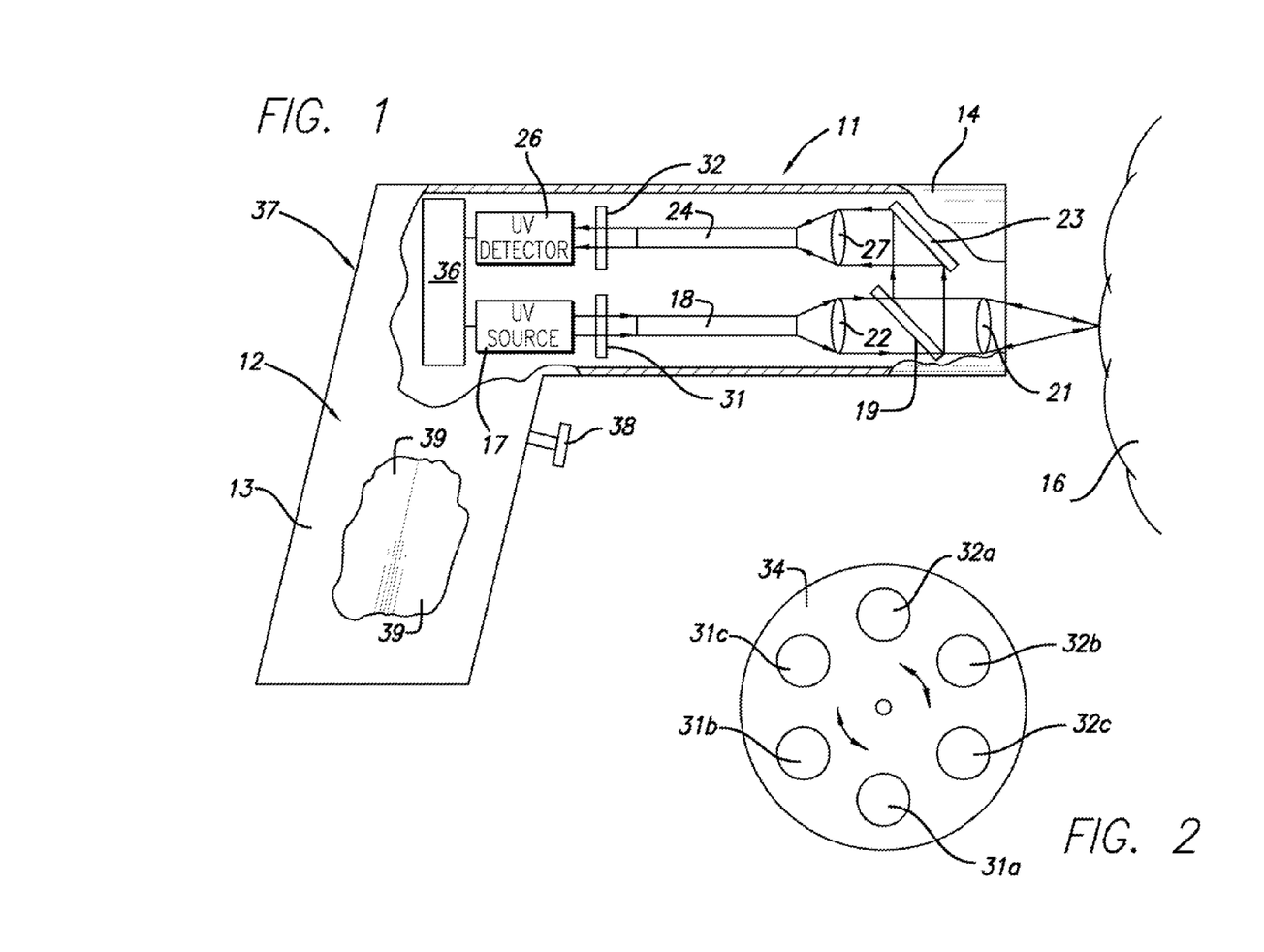
FIG. 1 is a side elevational view, partly broken away and somewhat schematic, of one embodiment of a handheld instrument for detecting pesticides on produce in accordance with the invention.
FIG. 2 is a side elevational view of a filter wheel for use in the embodiment of FIG. 1.

In the embodiment illustrated in FIG. 1, the instrument 11 has a housing 12 in the shape of a pistol, with a grip 13 which can be held in the hand of a user and a barrel 14 which can be pointed at produce 16 which is to be checked for the presence of pesticide residue. The produce can, for example, be a head of lettuce, an apple or any other fruit or vegetable.

An excitation source 17 is mounted within the housing for generating light which is directed onto the produce to induce fluorescent emission having a spectral content characteristic of the material that is emitting it. In this particular embodiment, the light source is a mercury vapor lamp which emits ultra-violet (UV) light at wavelengths of 254, 315 and 365 nanometers (nm). However, other types of light sources such as a xenon flashlamp can be utilized, if desired. The light source is located toward the rear of the barrel.

A bundle of one or more optical fibers 18 extends down the barrel from the light source toward a dichroic filter 19 and a focusing lens 21 near the front of the barrel, with another lens 22 between the fibers and the filter. The light passes through the dichroic filter and is focused on the target by the lenses.

The dichroic filter is reflective to the fluorescent emissions from the target, and those emissions are directed onto a mirror 23 which is positioned to one side of the filter near the front of the barrel.

A second bundle of one or more optical fibers 24 extends down the barrel from the mirror toward a UV detector 26, with a lens 27 between the mirror and the optical fibers for focusing emissions reflected by the mirror onto the fibers. The detector is located toward the rear of the barrel near the source.

Both the light from the source and the emissions from the target are filtered in order to maximize the emissions from the target and to make the instrument selectively responsive to emissions having a spectral content which is characteristic of the pesticide or pesticides to be detected. For that purpose, a first filter 31 is positioned between excitation source 17 and optical fibers 18, and a second filter 32 is positioned between optical fibers 24 and detector 26. Filter 31 is selected to pass light at a wavelength which induces the maximum fluorescent emission from the target for the pesticide to be detected, and filter 32 is selected to selectively pass emissions having a spectral content which is characteristic of that pesticide.

To detect different pesticides, a plurality of filters are mounted in pairs on a wheel 34 or other suitable carrier which can be moved to bring the filters for the desired pesticide into registration with the light source and detector. Thus for example, to detect the carbamate pesticides carbaryl, 1-Naphthol, and carbofuran, three sets of filters 31a-31c and 32a-32c can be provided. For carbaryl, the excitation maximum is near 270 nm and the emissions peak is around 320 nm, and filters 31a and 32a have passbands centered at those wavelengths. With 1-Naphthol the excitation maximum is near 280 nm, the emissions peak is around 340 nm, and filters 31b and 32b are centered at those wavelengths. For carbofuran, the excitation maximum is near 270 nm, the emissions peak is near 300 nm, and filters 31c and 31d are centered at those wavelengths.

Electronic circuitry 36 associated with the light source and the detector is mounted in the housing to the rear of the light source and detector. A display 37 for readings taken by the instrument is located at the rear of the barrel, and a trigger operated switch 38 for initiating readings is located in front of the grip. Memory for storing the readings is included in the circuitry, and batteries 39 for powering the instrument are mounted in the grip.

Figure 3:
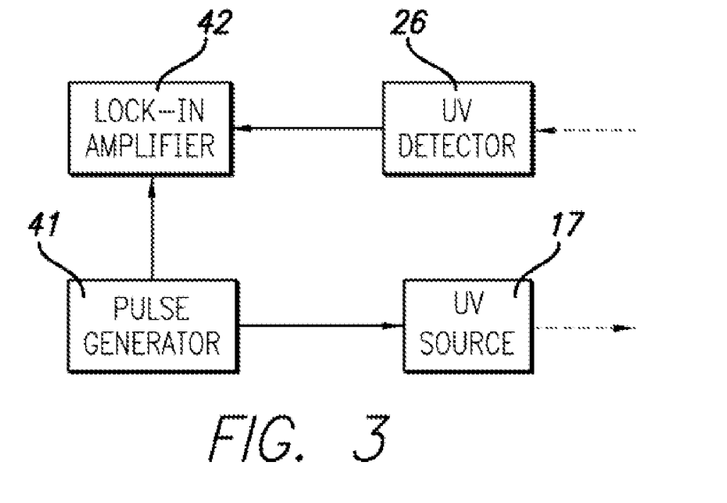
FIG. 3 is a simplified block diagram of the embodiment of FIG. 1.

In the embodiment illustrated in FIG. 3, circuitry 36 includes a pulse generator or clock 41 for controlling the operation of excitation source 17 to provide a pulsating light for exciting the target and a lock-in amplifier 42 for processing the signals from emissions detector 26. The clock signals or pulses which control the source are also applied to the reference input of the lock-in amplifier so that the detector output is, in effect, sampled in synchronization with the light from the source. This provides a high signal-to-noise ratio, particularly if the pulse rate is not an integral multiple of the local power line the frequency. Thus, for example, with 60 Hz power lines, a pulse rate of 90 Hz would be suitable.

Figure 4:
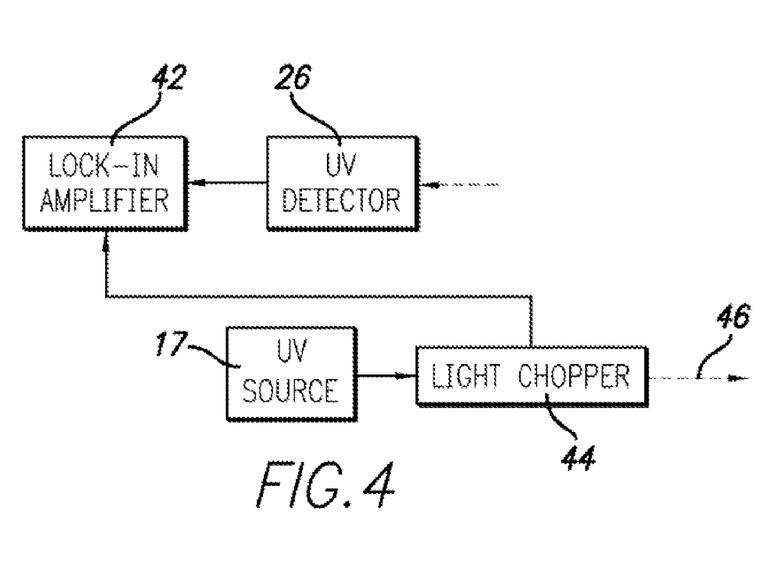
FIG. 4 is a simplified block diagram of another embodiment of a handheld instrument for detecting pesticides on produce in accordance with the invention.

In the embodiment of FIG. 4, the excitation source delivers a steady light output which is passed through a chopper 44 to produce a pulsating beam 46 that is directed onto the target. Signals from the emissions detector are processed by a lock-in amplifier 47 which is synchronized with the chopper to provide a high signal-to-noise ratio.

A pulsating beam can also be produced by the use of a stroboscopic source such as a Xenon flash lamp which produces one or more pulses of light.

Use of the instrument is simple and straightforward. The filter wheel is rotated to select the filters for the pesticide to be detected, the barrel is pointed at the target, and the trigger is pulled to take a reading. If residue of the pesticide is present, it will produce emissions which will be detected. The presence and/or approximate amount of the pesticide is indicated on the display and stored in memory.

Figure 5:
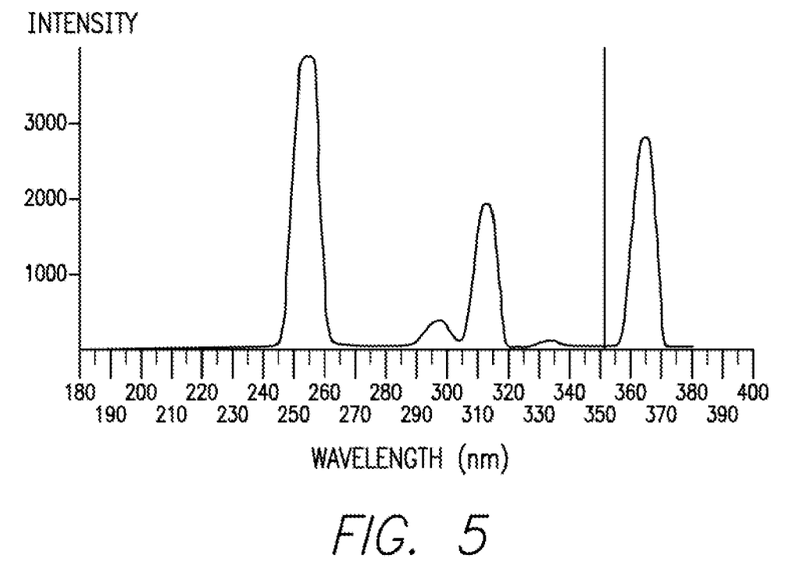
FIGS. 5-9 are response curves illustrating the detection of pesticide residue on produce in accordance with the invention.
Figure 6:
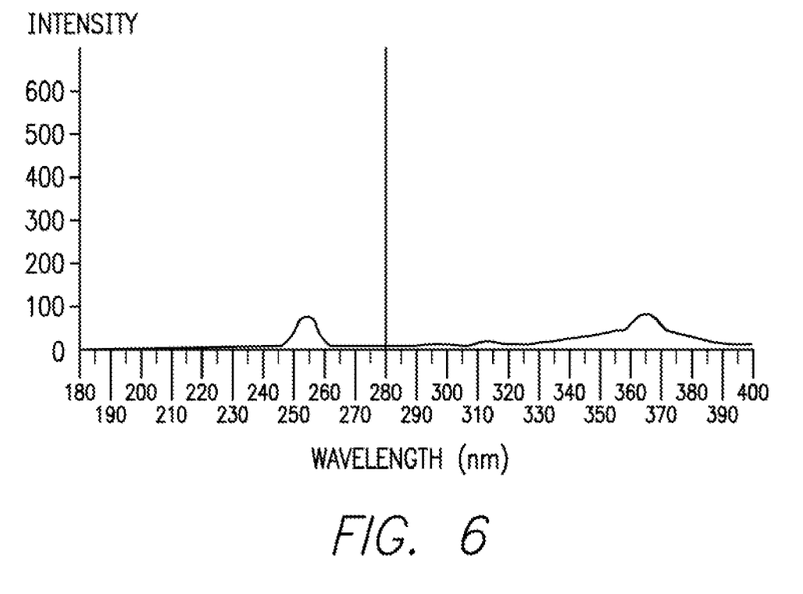
Figure 7:
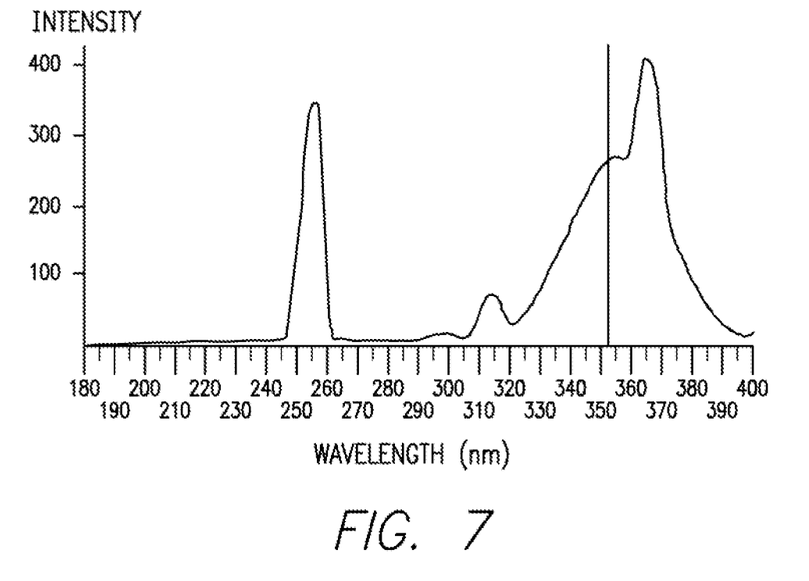
Figure 8:
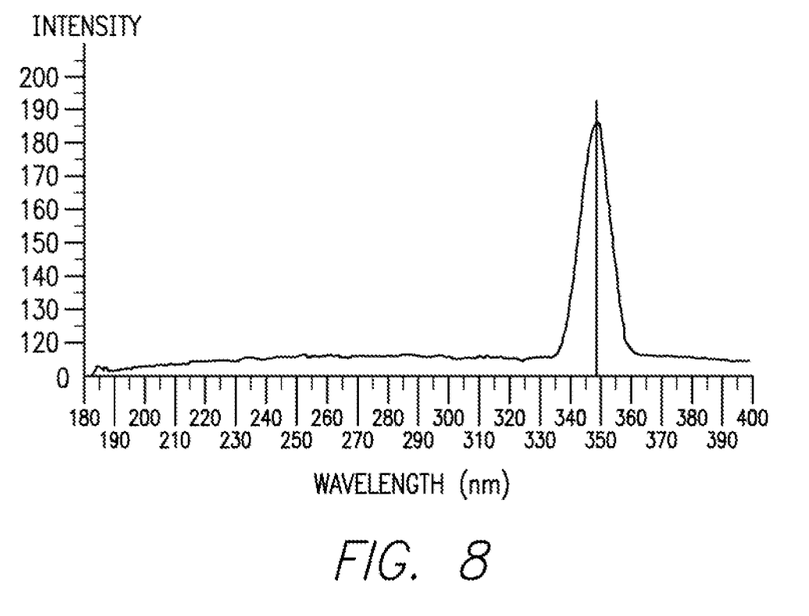
Figure 9:
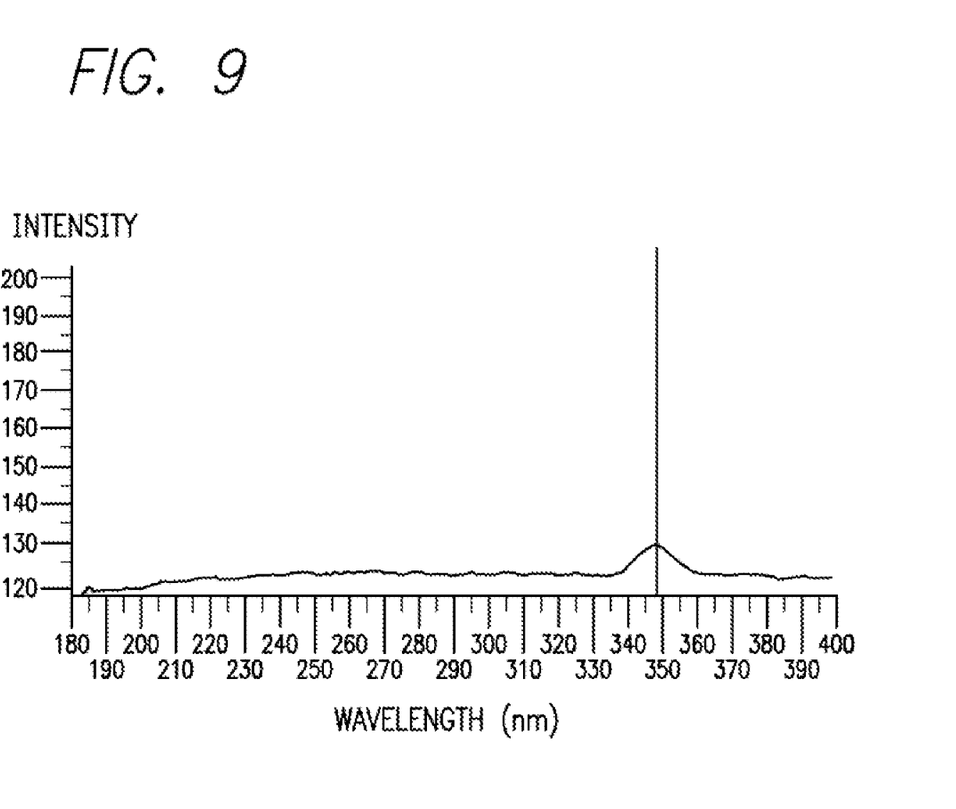

FIG. 5 shows the spectral content of the light from a mercury vapor lamp with peaks at 254 nm, 315 nm and 365 nm. FIG. 6 shows the spectral content of the fluorescent emissions which are produced by green lettuce without pesticide residue when illuminated with light from the mercury vapor lamp. FIG. 7 shows the result with the same light source and a carbamate pesticide, and FIG. 8 shows the result for the carbamate pesticide with a 350 nm filter in front of the detector. FIG. 9 shows the response produced by the green lettuce without pesticide residue with the 350 nm filter in front of the detector.

With the lettuce, there are no significant emissions in the spectrum of interest, and the weak responses centered at 254 nm, 315 nm, and 365 nm which appear in FIG. 6 are believed to be reflections of the excitation light by the lettuce. With the carbamate, the peaks from the source remain, but there is also a strong emission from the carbamate which is centered at about 353 nm. With the filter, everything is removed except the emission from the carbamate. Without the carbamate, the filter eliminates everything from the lettuce except the weak reflection of the excitation light around 350 nm.

Figure 10:
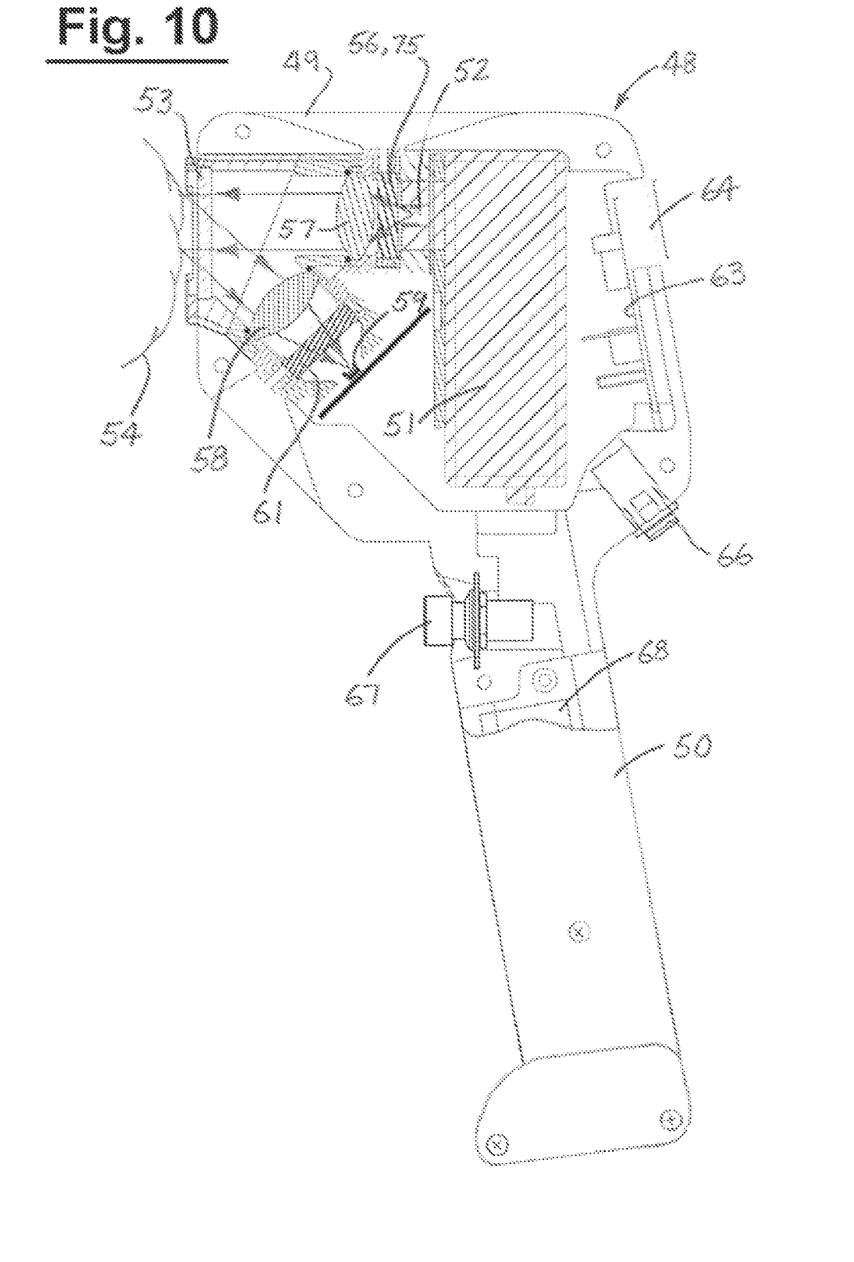
FIG. 10 is a side elevational view, partly broken away, of another embodiment of a handheld instrument for detecting pesticides in accordance with the invention.

FIG. 10 illustrates another embodiment in which the instrument includes a housing 48 with a head 49 and a handle 50 which depends from the head and can be gripped in the hand.

In this embodiment, the excitation source is a xenon flash unit 51 with a lamp 52 that produces high energy pulses of UV light over a broad spectrum of wavelengths. The flash unit is mounted in the head section of the housing, with flashlamp 52 facing in a forward direction toward a window 53 at the front of the housing. The window is fabricated of fused silica or another material which is transparent both to the excitation radiation and to radiation emitted from a target 54 in front of the instrument.

A bandpass filter 56 and a collimating lens 57 are positioned between the xenon flashlamp and the window. As in the embodiment of FIG. 1, the filter is selected to pass light at a wavelength which induces the maximum fluorescent emission from the target. The lens collimates the light and directs it through the window toward the target, illuminating an area having a diameter of about one inch in one current embodiment.

A focusing lens 58 directs fluorescent emissions from the target onto a UV detector 59, with a filter 61 between the lens and the detector. This filter is selected to selectively pass emissions having a spectral content which is characteristic of the pesticide to be detected. In this embodiment, there are no mirrors or dichroic elements, and the light passes directly from the source to the target and from the target to the detector, with the axis of the fluorescent emissions being inclined at an angle of about 45 degrees to the axis of the excitation beam.

The circuitry associated with the light source and the detector is mounted on a circuit board 63 toward the rear of the housing, and an output display 64 on the circuit board is visible through a window in the rear panel of the housing. An output jack 66 for delivering signals from the instrument to other instruments is located toward the rear of the housing below the panel. A trigger switch 67 for initiating readings is located on the front side of the handle, and batteries 68 for powering the instrument are housed in the handle.

Figure 11:
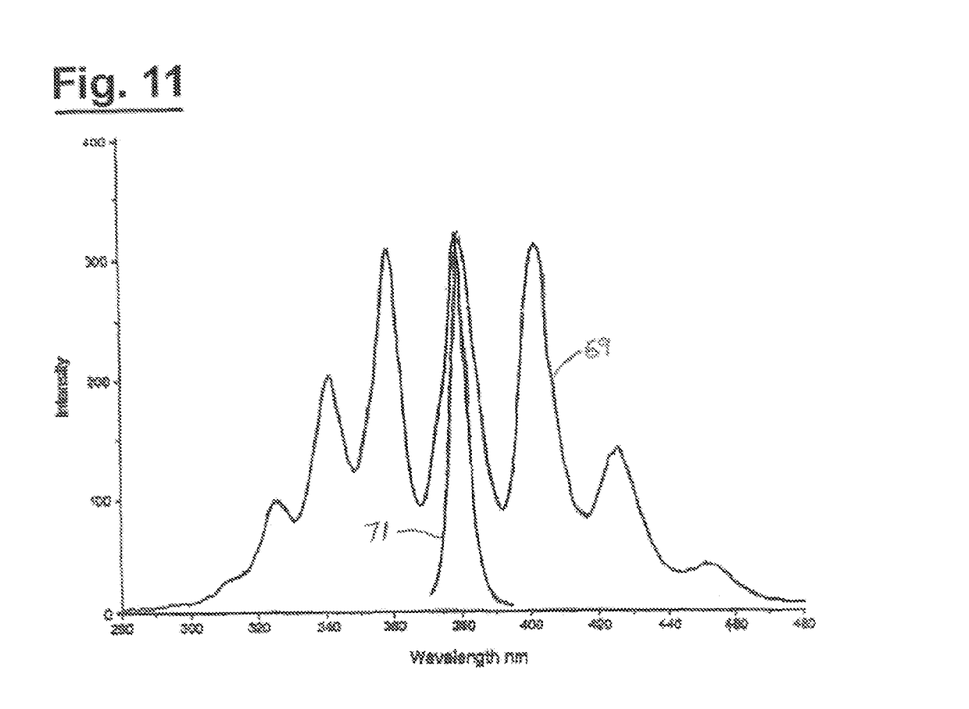
FIGS. 11 and 12 are emission and response curves illustrating the operation of the embodiment of FIG. 10.

Source filter 56 and detector filter 61 are mounted in a manner which permits them to be readily interchanged, and like the embodiment of FIG. 1, this embodiment can be utilized for detecting the residue from a variety of different pesticides simply by selecting the two filters in accordance with the spectral characteristics of the pesticide to be detected. Anthracene, for example, produces fluorescence emissions with major peaks at about 368, 380 and 402 nm when excited with UV light having a wavelength of about 380 nm, as illustrated by curves 69, 71 in FIG. 11. Thus, to detect anthracene, a source filter having a passband centered about 380 nm is used, and a detector filter having a passband centered about either 368 or 402 nm can be used.

Figure 12:
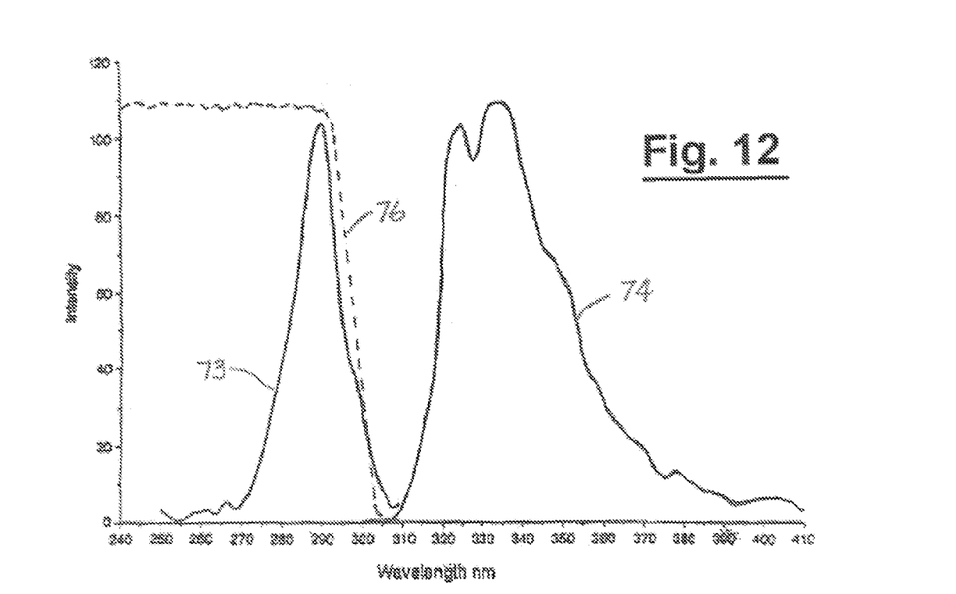

Similarly, as illustrated in FIG. 12, napthalene responds strongly to excitation at about 290 nm (curve 73), with fluorescence emissions ranging from about 305 nm to about 410 nm and peaking at about 330 nm (curve 74). Thus, for detecting napthalene, a source filter having a passband centered at about 290 is used in combination with a detector filter having a passband centered at about 330 nm.

There is, however, some overlap in the excitation and emission spectra between about 300 and 310 nm, which can cause "cross-talk" with excitation passing through to the detector and giving rise to false indications of napthalene when none is present. To prevent such false indications, a short pass filter 75 having a passband as shown by curve 76 can be positioned in front of or combined with source filter 56. The short pass filter has a cutoff frequency of about 300 nm and blocks excitation which overlaps with the emissions spectrum for napthalene and thereby prevents cross-talk from occurring.

The xenon flash unit can produce either a single pulse or a series of pulses of high peak power with relatively little drain on the batteries. When the xenon flash unit is used in combination with a detector that captures peak power, the instrument has a very high signal-to-noise ratio.

Rather than having source filter 56 and detector filter 61 disposed obliquely to each other, as they are in the embodiment of FIG. 10, they can be arranged in a coplanar fashion that facilitates inserting and changing the filters in pairs for the different pesticides. Thus, in the embodiment of FIG. 13, filters 56, 61 are mounted on a cartridge or slide 78 for insertion into and removal from the instrument as a unit. If desired, a short pass filter 75 can be included in the unit in addition to source filter 56. In this embodiment, collimating lens 57 is parallel to window 53 and oblique to filters 56, 75, with the axis of source 52 being perpendicular to the lens. Focusing lens 58 is oblique both to window 53 and to detector filter 61, with the axis of detector 59 being perpendicular to the detector filter.

Figure 14:
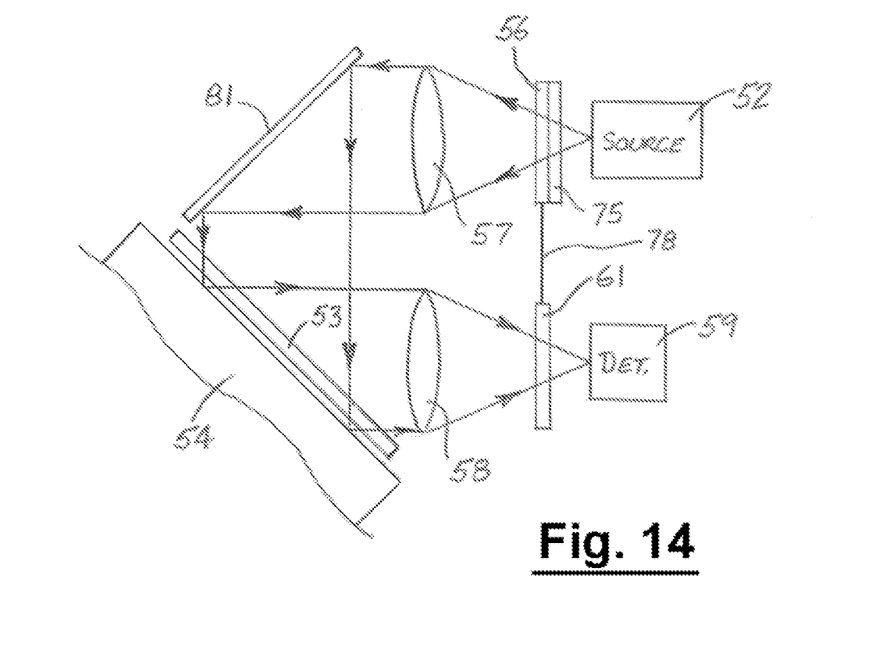

In the embodiment of FIG. 14, source filter 56 and detector filter 61 are once again mounted on a slide 78 along with short pass filter 75 (if used). Collimating lens 57 and focusing lens 58 are positioned side-by-side and parallel to the filters, with the axes of light source 52 and detector 59 being parallel to each other and perpendicular to the filters and lenses. A front surface mirror 81 is positioned to one side of and perpendicular to window 53 for reflecting collimated light from the source through the window toward target 54. Emissions from the target pass through the window directly to lens 61 and are focused on sensor 59.

Figure 15:
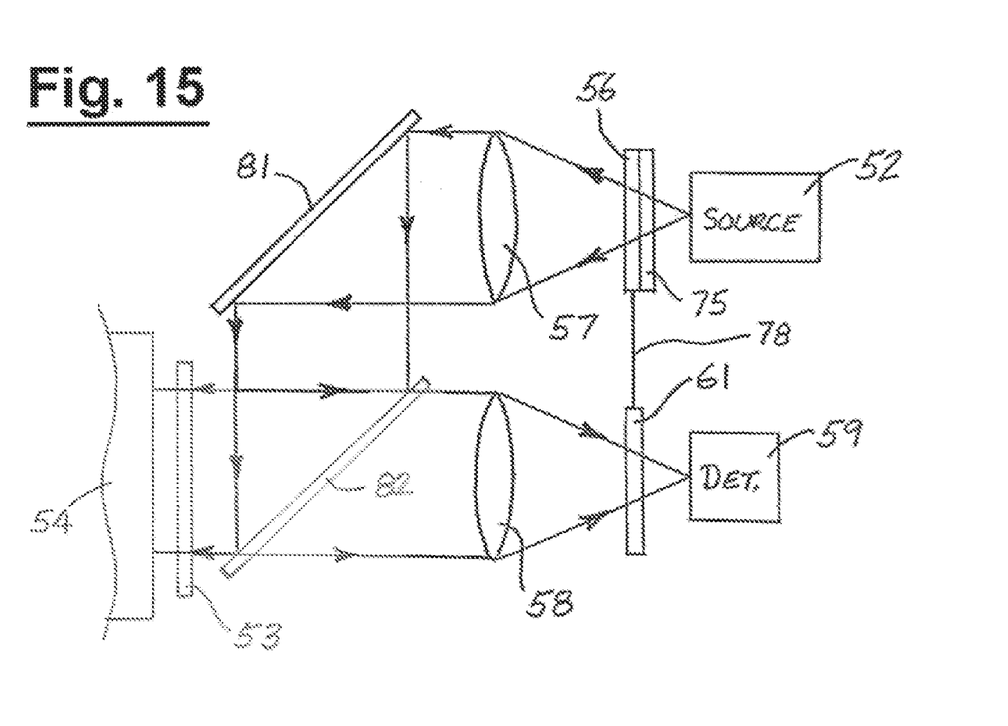

The embodiment of FIG. 15 is similar to the embodiment of FIG. 14 in that source filter 56 and detector filter 61 are once again mounted on a slide 78 along with short pass filter 75 (if used), with collimating lens 57 and focusing lens 58 positioned side-by-side and parallel to the filters, and the axes of light source 52 and detector 59 parallel to each other and perpendicular to the filters and lenses. In this embodiment, however, filters and lenses are also parallel to window 53, the axes of the light source and detector are perpendicular to the window, with the detector positioned in direct alignment with the window and the light source offset to one side of it.

Mirror 81 is once again positioned in the path of the collimated light from light source 52 and collimating lens 57, but a dichroic filter 82 is positioned between window 53 and focusing lens 58. This filter is reflective to the light from the source and transmissive to the fluorescent emissions from the target.

Thus, in the embodiment of FIG. 15, light from source 52 passes through filters 75 and 56 and is collimated by lens 57 and directed onto mirror 81. The collimated light is reflected by the mirror onto dichroic filter 82 which reflects the light through window 53 and onto target 54. Emissions from the target pass directly through the window and the dichroic filter and are focused onto detector 59 by focusing lens 58.

Figure 13:
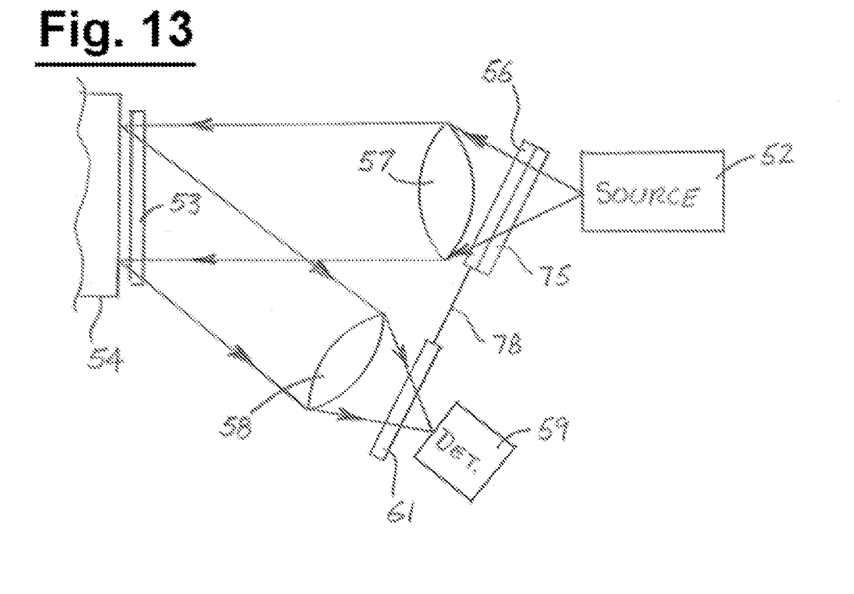
FIGS. 13-15 are diagrams of other optical systems which can be utilized in the embodiment of FIG. 10.

This embodiment has an advantage over the embodiments of FIGS. 13 and 14 in that the axes of both the light source and the detector are perpendicular to the target, rather than one or both of them being oblique to it. It may also permit a more compact arrangement of the optical elements than some of the other embodiments, and it may also allow the light source and the detector to be held closer to the target.

The invention has a number of important features and advantages. It provides a highly portable, self-contained, battery powered instrument which can detect the presence of pesticide residue instantly and without contact with the produce. It can be used in the field as well as by distributors and at super markets to determine pesticide content.

It is apparent from the foregoing that a new and improved instrument and method for detecting and identifying pesticides on lettuce and other produce has been provided. While only certain presently preferred embodiments have been described in detail, as will be apparent to those familiar with the art, certain changes and modifications can be made without departing from the scope of the invention as defined by the following claims.

The invention claimed is:

1. A handheld instrument for checking produce for pesticide residue, comprising: a housing, a window in a wall of the housing, an excitation source and an emission detector within the housing, a collimating lens for directing a beam from the source through the window onto produce in proximity to the housing to induce fluorescent emissions from pesticide residue on the produce, and a focusing lens within the housing for focusing the emissions from the produce on the detector.

2. The instrument of claim 1 including a filter within the housing for selectively passing emissions having a spectral content characteristic of the pesticide to be detected to the detector.

3. The instrument of claim 1 including a filter within the housing for selectively passing light from the source of a wavelength which induces maximum fluorescent emission from the pesticide to be detected.

4. The instrument of claim 1 including a short pass filter between the source and the collimating lens for blocking light having a wavelength in the same range as the emissions from the pesticide.

5. The instrument of claim 1 wherein the excitation source includes a xenon flashtube.

6. The instrument of claim 1 further including circuitry within the housing for processing signals from the detector, and a battery in the housing for powering the excitation source and the processing circuitry.

7. The instrument of claim 1 wherein the beam from the source and the emissions from the pesticide pass directly between the lenses and the produce with no other optical elements between the lenses and the window.

8. The instrument of claim 1 including a mirror within the housing for reflecting the beam from the source through the window and onto the produce.

9. The instrument of claim 1 including a mirror for reflecting light from the excitation source, and a dichroic filter for reflecting light from the mirror onto the target and passing the fluorescent emissions from the target to the focusing lens.

10. The instrument of claim 9 wherein the focusing lens and the detector are aligned axially with the window, and the excitation source, the collimating lens and the mirror are offset axially from the mirror.

11. A handheld instrument for checking produce for pesticide residue, comprising: a housing, a window in a wall of the housing which can be held in proximity to the produce, an excitation source and an emission detector within the housing, a collimating lens for directing a beam of light from the source through the window onto the produce to induce fluorescent emissions from pesticide residue on the produce, a first filter positioned in the path of the light for selectively passing light of a wavelength which induces maximum fluorescent emission from the pesticide to be detected, a focusing lens within the housing for focusing emissions from the produce on the detector, and a second filter positioned in the path of the emissions for selectively passing emissions having a spectral content characteristic of the pesticide to be detected to the detector.

12. The instrument of claim 11 wherein the first filter is positioned between the source and the collimating lens.

13. The instrument of claim 11 wherein the second filter is positioned between the focusing lens and the detector.

14. The instrument of claim 11 including an additional filter positioned in the path of the light from the source for blocking light having a wavelength which overlaps with the wavelengths of emissions from the pesticide.

15. The instrument of claim 14 wherein the additional filter is a short pass filter which passes light having wavelengths below a predetermined length.

16. The instrument of claim 11 wherein the excitation source includes a xenon flashtube.

17. The instrument of claim 11 further including circuitry within the housing for processing signals from the detector, and a battery in the housing for powering the excitation source and the processing circuitry.

18. The instrument of claim 11 wherein the first and second filters are mounted on a carrier for insertion and removal as a unit into and from the paths of the light from the source and the emissions from the produce.

19. The instrument of claim 18 wherein the filters are generally coplanar of each other.

20. A method of checking produce for the presence of pesticide residue, comprising the steps of: holding a portable, handheld instrument in proximity to the produce to be checked, passing light from a source within the instrument through a collimating lens to form a beam which is directed onto the produce to induce fluorescent emission from pesticide residue on the produce, and passing fluorescent emissions from the produce through a focusing lens onto a detector within the instrument to detect the presence of pesticide residue on the produce.

21. The method of claim 20 including the step of filtering the emissions from the produce to selectively pass emissions having a spectral content characteristic of the pesticide to be detected.

22. The method of claim 20 including the step of filtering the light from the source to selectively pass light of a wavelength which induces maximum fluorescent emission from the pesticide to be detected.

23. The method of claim 22 including the step of filtering the light from the source to block light having a wavelength in the same range as emissions produced by the pesticide.

\* \* \* \* \*